United States Patent [19]
Edlund

[11] Patent Number: 5,498,278
[45] Date of Patent: Mar. 12, 1996

[54] COMPOSITE HYDROGEN SEPARATION ELEMENT AND MODULE

[75] Inventor: David J. Edlund, Redmond, Oreg.

[73] Assignee: Bend Research, Inc., Bend, Oreg.

[21] Appl. No.: 359,917

[22] Filed: Dec. 19, 1994

Related U.S. Application Data

[63] Continuation-in-part of Ser. No. 148,999, Nov. 8, 1993, Pat. No. 5,393,325, which is a continuation-in-part of Ser. No. 986,692, Dec. 7, 1992, Pat. No. 5,259,870, which is a continuation-in-part of Ser. No. 566,092, Aug. 10, 1990, abandoned.

[51] Int. Cl.[6] .................................................. B01D 53/22
[52] U.S. Cl. ................................. 96/11; 95/56; 55/524
[58] Field of Search ........................ 95/55, 56; 96/4, 96/7, 8, 10, 11

[56] References Cited

U.S. PATENT DOCUMENTS

| | | | |
|---|---|---|---|
| 2,958,391 | 11/1960 | de Rosset | 95/56 |
| 3,238,703 | 3/1966 | Straschil et al. | 96/4 |
| 3,238,704 | 3/1966 | Straschil et al. | 96/11 |
| 3,447,288 | 6/1969 | Juda et al. | 55/158 |
| 3,469,372 | 9/1969 | Yamauchi et al. | 96/11 |
| 3,486,301 | 12/1969 | Bonnet | 96/7 |
| 3,738,813 | 6/1973 | Esmond | 96/4 X |
| 4,014,657 | 3/1977 | Gryaznov et al. | 96/7 X |
| 4,134,742 | 1/1979 | Schell | 95/55 X |
| 4,468,235 | 8/1984 | Hill | 55/16 |
| 4,496,373 | 1/1985 | Behr et al. | 55/16 |
| 4,699,637 | 10/1987 | Iniotakis et al. | 55/158 |
| 4,857,080 | 8/1989 | Baker et al. | 95/56 |
| 5,126,045 | 6/1992 | Kohlheb et al. | 96/4 X |

FOREIGN PATENT DOCUMENTS

| | | |
|---|---|---|
| 1238866 | 7/1988 | Canada . |
| 4-386824 | 12/1992 | Japan . |
| 5-076738 | 3/1993 | Japan . |
| 1325426 | 8/1973 | United Kingdom ........ 95/56 |
| WO 09231 | 8/1923 | WIPO . |

OTHER PUBLICATIONS

Gryaznov, et al, *Applied Catalysis A: Gener L*, 96 (1993) 15–23.
Hsieh, 33 *Catal Rev. Sci. Eng. I.* (1991) 1–70.
Sermon et al., 72 *JCS Faraday Trans. I.* (1976) 730–744.
Gavalas et al., 44 *Chem. Eng. Sci.* (1989) 1829–1835.

*Primary Examiner*—Robert H. Spitzer
*Attorney, Agent, or Firm*—Chernoff, Vilhauer, McClung & Stenzel

[57] ABSTRACT

There are disclosed improvements in multicomponent composite metal membranes useful for the separation of hydrogen, the improvements comprising the provision of a flexible porous intermediate layer between a support layer and a nonporous hydrogen-permeable coating metal layer, and the provision of a textured coating metal layer.

34 Claims, 7 Drawing Sheets

COMPOSITE HYDROGEN SEPARATION ELEMENT AND MODULE

The government has rights in this invention pursuant to Grant Nos. ISI-8722212 awarded by the National Science Foundation and DE-FG03-91ER81228 and DE-FG03-91ER81229 awarded by the Department of Energy.

This is a continuation-in-part of application Ser. No. 08/148,999 filed Nov. 8, 1993 now U.S. Pat. No. 5,393,325, which is a continuation-in-part of application Ser. No. 07/986,692 filed Dec. 7, 1992, now U.S. Pat. No. 5,259,870, which is a continuation-in-part of application Ser. No. 07/566,092, filed Aug. 10, 1990, now abandoned.

BACKGROUND OF THE INVENTION

Membranes and membrane modules for separation of hydrogen from other gases are known. See Zolandz et al. at pages 95–98 in *Membrane Handbook* (1992). In particular, useful membranes for hydrogen separations are of four types: polymeric, porous ceramic, self-supporting nonporous metal, and nonporous metal supported on a porous rigid matrix such as metal or ceramic.

Polymeric membranes are commonly used in the form of extended flat sheets or small diameter hollow fibers. Flat sheet polymeric membranes are most often incorporated into spiral-wound modules. In this case, the membrane forms an envelope around a flexible polymeric or cloth net (the permeate spacer). The edges of the membrane are glued together to form a gas-tight seal that separates the feed gas, which flows over the outer surface of the membrane envelope, from the permeate gas, which is collected in the cavity created by the permeate spacer. The permeate spacer forms a continuous channel connecting to a permeate collection tube that allows the permeate hydrogen to flow through the permeate spacer and into the permeate collection tube.

Hollow fiber membranes are incorporated into hollow-fiber modules which are very similar in design to shell-and-tube heat exchangers. Polymeric adhesives and sealants such as epoxy resins are used to seal the tubular or hollow fiber membranes into the module shell to form a gas-tight barrier. This allows the gas to be fed to either the interior or exterior of the fibers, thereby preventing gas from flowing into the permeate stream except by permeation through the fiber wall. In cases where the feed gas is directed to the interior of the fibers the hydrogen permeate is collected on the "shell" side or outside of the tubes or fibers.

Polymeric membranes and membrane modules for hydrogen separations suffer from a lack of high selectivity toward hydrogen over other gases resulting in a relatively impure product gas, a lack of stability at operating temperatures above 250° C., and chemical incompatibility with many chemicals such as hydrocarbons that are present in the impure hydrogen feed stream. To overcome these limitations, highly selective and more robust materials must be used for the hydrogen separation membrane and for sealing the membrane into the membrane module.

Inorganic materials, notably nonporous and porous ceramics and nonporous or dense metals, are known to make robust hydrogen-selective diffusion membranes. Such inorganic membranes are suitable for use at temperatures above 250° C. and are not damaged by many chemicals, including hydrocarbons.

Nonporous inorganic oxides are known to be permeable to hydrogen in its ionic form. For example, U.S. Pat. No. 5,094,927 discloses materials that are permeable to hydrogen ions (referred to as "solid-state proton conductors") based on silicon oxide, oxides of Groups IVB, VB, VIB and VIII of the Periodic Table, and fluorides of Groups IIA and IIIB of the Periodic Table. Additionally, diffusion coefficients for hydrogen ions through the oxides of molybdenum and tungsten have been reported by Sermon et al. in 72 *JCS Faraday Trans. I* 730 (1976).

Such solid-state proton conductors have been used by placing them between the cathode and anode in fuel cells, resulting in a net transport of hydrogen between the cathode and anode. However, these solid-state proton conductors are generally brittle, exhibit relatively low permeability to hydrogen, and have not generally been reported for use as a hydrogen separation membrane. The one exception is a nonporous silicon oxide membrane that is reported to allow hydrogen permeation through the silicon oxide by an activated surface-transport mechanism along grain boundaries. See Gavalas et al., 44 *Chem. Eng. Sci.* 1829 (1989). Although this dense silicon oxide membrane exhibits very high selectivities for hydrogen relative to nitrogen, it is also brittle and susceptible to reaction with steam at elevated temperatures, further limiting its utility.

Exemplary materials that have been investigated for use as porous inorganic molecular hydrogen-permeable membranes include aluminum oxide, silicon oxide, titanium oxide, magnesium oxide, chromium oxide, tin oxide, and various zeolites. See, for example, Hsieh, 33 *Catal. Rev. Sci. Eng.* 1 (1991). While such membranes exhibit very high hydrogen permeability, they also suffer from very low hydrogen selectivity due to their relatively large mean pore diameter and, as with the nonporous hydrogen-permeable ceramics discussed above, porous ceramics are also very brittle by nature and so are susceptible to failure due to cracking.

Porous ceramics, typically alpha- or gamma-aluminum oxide in the form of tubes, separate hydrogen from other gases based on differential gas phase diffusion rates through the pores of the ceramic. Such ceramic membranes are typically incorporated into a shell-and-tube module. A seal between the ceramic tube and the module shell, to prevent the feed gas from flowing directly into the permeate stream, is made by one of two methods: (1) polymeric o-rings are used to make the seal outside of any heated zone of the membrane module; or (2) graphite string or cord is used with metal compression fittings to make the seals within the heated zone of the membrane module. The use of polymeric sealing materials requires that the ends of the membrane module be kept cool, which is difficult when large volumes of gas are flowing through the module. Because these porous ceramic membranes have relatively low selectivity for hydrogen over other gases, the integrity of the seals is often difficult, if not impossible, to assess.

To overcome the inherently low selectivity of porous ceramic membranes, palladium- or palladium-alloy-coated ceramic membranes have been disclosed. See Hsieh, "Inorganic Membrane Reactors," 33 *Catal. Rev Sci. Eng.* 1 (1991). Since nonporous or dense layers of hydrogen-permeable metals such as platinum, palladium, nickel and certain alloys thereof are permeable only to hydrogen, the selectivity for hydrogen over other gases is very high, which is a desirable characteristic of membrane-based separations. Such metal-coated ceramic membranes are typically incorporated into shell-and-tube modules using graphite gaskets within a compression fitting to seal the membrane tube to the module, thereby to prevent gas flow from the feed stream directly to the permeate stream. However, the large differences between the coefficient of thermal expansion of the ceramic tube and of the metal compression fitting, combined with the brittleness of the ceramic tube, results in a high frequency of leaks between the feed stream and the permeate stream at the gasket. See J. P. Collins, "Preparation and Characterization of a Composite Palladium-Ceramic Membrane," 32 *Ind. Eng Chem. Res* 3006 (1993). Another drawback of ceramic-supported thin metal foil membranes is that the metal foil is subject to macroscopic ruptures should the ceramic crack due to uneven loading or to thermal or mechanical shock.

Nonporous metal membranes that are selectively permeable to hydrogen are also known. See, for example, U.S. Pat. Nos. 4,388,479 and 3,393,098, both of which disclose Group VIIB and VIII alloy membranes such as palladium alloy catalytic membranes. Such metal membranes are superior to polymeric membranes and to inorganic (non-metal) membranes in that they have essentially complete selectivity for hydrogen over other gases, can be operated at temperatures up to about 1000° C., and are chemically resistant to gases in the feed stream. However, the prohibitively high cost of palladium has led to efforts to fabricate composite hydrogen-permeable metal membranes by coating certain less expensive transition metal alloy base metals with palladium or palladium alloys. See, for example, U.S. Pat. Nos. 4,468,235 and 3,350,846. The palladium or palladium-alloy coating on such base metals employs only a relatively small amount of palladium, imparting chemical resistance to the base metal and in some cases increasing the rate of adsorption of hydrogen onto the metal membrane surface.

U.S. Pat. No. 2,958,391 describes a metal membrane module consisting of a palladium or palladium alloy supported directly on a porous base metal comprising a sintered-metal matrix. The sintered-metal matrix may be in the shape of a flat plate or an elongated cylinder. Hydrogen permeates from the external surfaces of the palladium or palladium alloy membrane into the porous sintered-metal matrix, is conducted through its pore structure, and is collected.

In addition to porous ceramic and sintered-metal supports for hydrogen-permeable metal membranes, U.S. Pat. Nos. 3,477,288 and 4,699,637 disclose the use of a metal mesh or gauze to support the thin metal membrane. Means to fabricate membrane modules are not taught in these patents. However, Canadian Patent No. 1,238,866 describes the use of a silver-based solder to seal to the module the edges of a flat-sheet palladium alloy membrane supported on a metal mesh or gauze, porous sintered metal, or perforated metal.

However, such coated or supported metal membranes have an inherent shortcoming in that, under the elevated temperature conditions of use, the coating metal tends to diffuse into the base metal or porous metal support, thereby destroying both the hydrogen permeability and the chemical resistance available from such composite metal membranes. U.S. Pat. No. 4,496,373 discloses a nonporous hydrogen-permeable composite metal membrane that addresses this intermetallic diffusion problem for a base metal alloy of a specific composition coated with a palladium alloy of specific composition. However, the composition of the palladium alloy coating and the base metal alloy are narrowly defined so as to favor partitioning of the palladium into the coating alloy as opposed to the base metal alloy. Consequently, this approach is not general in nature, requires strict control over alloy composition, and allows for little variation in selection of metals for membrane fabrication.

A general approach to preventing intermetallic diffusion in composite metal membranes, disclosed in commonly owned U.S. Pat. No. 5,259,870 and application Ser. No. 08/148,999, is to utilize a chemically and thermally stable intermediate layer between a coating metal layer and a dense hydrogen-permeable base metal. The coating metal layer comprises a dense (i.e., non-porous), hydrogen-permeable metal including palladium and palladium alloys. The base metal layer is also a dense, hydrogen-permeable metal and is selected from the metals found in Groups 3 through 5 of the Periodic Table and their hydrogen-permeable alloys. The intermediate layer (also called the intermetallic diffusion barrier) includes chemically and thermally stable oxides (e.g., aluminum oxide and silicon oxide) and serves to prevent direct contact between the coating metal layer and the base metal layer.

Japanese Laid-Open Application Nos. 346,824/92 and 76,738/93 both disclose a hydrogen gas separation membrane comprising a thin membrane of palladium, a porous metal support and a ceramic or metal oxide barrier layer between the palladium and the support. However, the barrier layer is inherently rigid and brittle.

PCT application No. 90/09231 discloses a hydrogen separation membrane comprising an inorganic support having interstices, the interstices of the support being bridged by a composite layer of partially sintered non-metallic particles and a hydrogen-permeable metal such as palladium, the bridging taking place in such a fashion as to render the composite layer coplanar with the support.

In all of these approaches to using an oxide layer to limit or prevent intermetallic diffusion in a composite metal membrane, the oxide layer is inherently brittle. Thus, membranes made according to these teachings are subject to failure due to formation of pinholes, cracks, and/or tears in the coating metal layer as a result of fracture of the brittle oxide layer directly beneath the coating metal layer.

The use of a chemically reactive intermediate oxide layer in hydrogen-permeable metal membranes is also known. In contrast to the chemically and thermally stable intermediate layers described above, such a reactive oxide layer facilitates, rather than prevents, intermetallic diffusion. For example, Russian Patent No. 1,058,587 discloses a method for manufacturing membrane elements for diffusion-based hydrogen separators by diffusion-welding palladium or palladium-alloy membranes to an undefined metal substrate. Specifically, the '587 patent discloses first saturating a hydrogen-permeable coating metal at elevated temperature, then cooling the so-hydrogen-loaded coating metal, then applying a "reactive gasket" of ultrafinely divided powders of metallic oxides over the area between a base metal and the coating metal where the base and coating metals are to be welded together, then subjecting the composite to high pressure (2000–2500 psi) and high temperature (650°–700° C.) to achieve a "diffusion weld" between the coating metal and the base support metal. The diffusion weld results from the complete reduction of the metal oxides "reactive gasket" intermediate layer to pure metal(s) by hydrogen desorbed from the hydrogen-loaded coating metal. It is unclear whether (1) the palladium or palladium-alloy membrane is attached only to the edges of the metal substrate via the diffusion-bonded weld, or (2) the palladium or palladium-alloy membrane completely covers the surface of the metal substrate and the diffusion-bonded weld. In the first case, the welded portion of the membrane need not be hydrogen-permeable, as hydrogen is required only to permeate the unwelded portion of the palladium or palladium-alloy membrane and the hydrogen-permeable portion of the membrane is not a composite metal membrane at all, but rather is simply a palladium or palladium-alloy membrane. The drawback of such an approach is that the palladium or palladium-alloy membrane must be sufficiently thick to be self-supporting and the membrane is therefore unacceptably expensive. In the second case, the resulting composite membrane would include an intermediate layer which, after fabrication, is a metal or metal alloy, with attendant reduction in the overall hydrogen permeability of the membrane.

Despite the fact that hydrogen-permeable metal membranes were first commercialized nearly three decades ago, practical and affordable metal membrane modules are still lacking. Known module designs suffer from high cost due to complex configurations and permanent assembly methods that make repairs difficult and expensive, reduced membrane permeability due to interdiffusion of metallic constituents from the metal support matrix or from the module itself, and breakdown of the membrane due to damage to the coating metal layer arising from dimensional changes in the membrane under the conditions of use. The present invention overcomes these and other shortcomings of the prior art.

SUMMARY OF THE INVENTION

The present invention comprises a composite hydrogen-permeable inorganic membrane and a module incorporating the membrane, both of which are capable of accommodating dimensional changes in the coating metal layer that occur in use, which prevents damage to both the coating metal and intermediate layers. The membrane comprises three elements: (1) a chemically and thermally stable porous intermediate layer between (2) a hydrogen-permeable coating metal layer and (3) a rigid support matrix. The keys to the accommodation of dimensional changes in the coating metal layer have been found to lie in the provision of (1) a flexible non-sintered intermediate layer, preferably a woven or non-woven fabric; or (2) a textured coating metal layer wherein the texture is retained during use; or a combination of (1) and (2).

The rigid support matrix lends tensile strength to the composite metal membrane and so must be chosen with this in mind. Also, hydrogen must pass through the support matrix relatively unimpeded. A wide range of materials may be used as the support matrix, including dense, hydrogen-permeable metals; porous, perforated, and slotted metals that need not be permeable to hydrogen; and porous, perforated, and slotted ceramics.

When the support matrix is a metal or metal alloy (either a dense hydrogen-permeable metal or a porous, perforated or slotted metal), the provision of a flexible porous non-sintered intermediate layer (1) prevents intermetallic diffusion between the support matrix and the coating metal layer; (2) accommodates dimensional changes of the coating metal layer by expanding and contracting; and (3) establishes a conduit or pathway for hydrogen flow to any permeable portions of the support matrix.

The provision of a textured coating metal layer allows accommodation of the natural expansion and contraction of that layer during use in such a manner as to prevent the formation of pinholes, cracks, tears and the like that would otherwise lead to mechanical failure of the coating metal layer.

DETAILED DESCRIPTION OF PREFERRED EMBODIMENTS

The overall composite membrane is selectively permeable to hydrogen gas and may be used in conventional fashion to separate hydrogen from other gases such as nitrogen, carbon monoxide, carbon dioxide, hydrogen sulfide, steam, ammonia or hydrocarbons such as methane, ethane, propane or olefins, by conventional methods, the essential features of which comprise contacting a feed gas containing hydrogen and other gases at temperatures generally exceeding 200° C. and at a hydrogen partial pressure on the feed side of the membrane that is elevated relative to the hydrogen partial pressure on the permeate side of the membrane, allowing the selective permeation of hydrogen through the composite membrane, and collecting the permeated hydrogen. Since the membrane is selectively permeable to hydrogen even at temperatures of less than 200° C., such as at ambient temperatures (0° to 50° C.), the membrane has utility for separating hydrogen even at these lower temperatures, subject only to economic limitations, since the hydrogen permeability of the membrane is reduced at lower temperatures. Also, the permeate hydrogen need not be collected, but may be oxidized to form water or removed from the permeate side of the membrane with a sweep stream. The composite membrane is also useful in hydrogen separation methods such as are disclosed in U.S. Pat. No. 5,217,506. The hydrogen selectivity of the composite membrane is outstanding, exhibiting a selectivity of $\geq 100$ with a flux of $\geq 0.001$ $m^3/m^2 \cdot hr$ at 400° C. and 100 psig hydrogen feed side pressure with the partial pressure of hydrogen on the permeate side at ambient pressure.

The composite membrane of the present invention is particularly stable under conditions of elevated temperature. Specifically, when exposed to a 100 psig hydrogen feed stream of $\geq 99.95\%$ purity at $\geq 400°$ C., with ambient pressure on the permeate side, the composite membrane retains ≧20% of its initial flux over a continuous period of up to 250 days at 400° C. and up to 60 days at 600° C. As shown herein, this stability is directly attributable to the presence of the intermediate layer.

The support matrix is preferably ceramic or metal or carbon and serves two functions. First, it provides mechanical support to the thin metal membrane and the flexible intermediate layer so that the module can be operated with a large transmembrane pressure such as 10–600 psig difference between the feed and permeate pressures. Second, the matrix must allow hydrogen to pass relatively unimpeded through the multilayer composite membrane. As mentioned previously, the support matrix can be either a dense (nonporous) hydrogen-permeable metal or a material that has passages through which hydrogen can pass. In the latter case, the matrix contains continuous channels or pore structure that serves to collect the permeate hydrogen. The channels or pore structure of the support matrix are sufficiently large to minimize pressure drop as the permeate hydrogen flows through the support matrix to a collection tube or channel.

The rigid support matrix of the composite membrane provides mechanical support to the membrane and, as such, is selected primarily for its mechanical properties. For flat-sheet membranes the support matrix is preferably a perforated metal sheet, a slotted metal sheet, a porous sintered-metal sheet, or a metal mesh. For tubular membranes the support matrix is preferably a perforated metal tube, a porous sintered-metal tube, or a tube comprising a metal mesh. For both flat-sheet and tubular membranes the support matrix may also be dense and continuous (i.e., nonporous and without holes or perforations through the metal), provided that the coating metal and the flexible intermediate layer extend up to, or slightly beyond, the edges of the support matrix such that hydrogen permeating the coating metal may flow through the intermediate layer roughly parallel to the coating metal surface and around the edge of the support matrix.

Alternatively, the dense support matrix can be composed of a hydrogen-permeable material such as an alloy of the Group 3 through 5 metals, palladium, or nickel such that the hydrogen can pass directly through the matrix. When the support matrix has passageways through or around it, its chemical nature is of little significance so long as it does not react with either hydrogen or with the intermediate layer to cause a substantial decrease in the hydrogen flux through the composite membrane or to substantially weaken the composite membrane. For instance, the support should not comprise a metal or alloy that is severely embrittled in the presence of hydrogen under operating conditions. However, as mentioned above, the support may be permeable to hydrogen in the sense that hydrogen dissolves and diffuses through it. Stainless steel, due to its strength, availability, and low cost, is a preferred material for use as the support. In the practice of the present invention, the thickness of the support is largely unimportant as long as the foregoing condition that it not impede hydrogen permeation is met.

The coating metal is preferably at least one hydrogen-permeable metal that may be a transition metal or alloy or composite thereof. It should be chemically and physically stable at temperatures of at least 200° C., and is preferably selected from the transition metals of Groups VIIB and VIIIB of the Periodic Table, most preferably Fe, Mn, Ni, Pd, Pt, Ru, and hydrogen-permeable alloys containing ≧20 wt % of said metals. For example, an alloy comprising 10–50 atom % silver, the remainder comprising palladium, is particularly preferred for applications wherein the feed contains <10 ppm sulfur. The coating metal layer is dense and continuous in the sense that it is not porous and does not contain holes, cracks, or other breaks that span the thickness of the metal layer, and is preferably from 0.1 to 75 µm in thickness.

The coating metal layer of metal membranes often experiences dimensional changes due to changes in operating conditions such as temperature, hydrogen partial pressure, and transmembrane pressure. For instance, a coating metal layer comprising an alloy of palladium with 25% silver expands about 3% when exposed to hydrogen under typical hydrogen separation conditions. To avoid damage to either the coating metal or intermediate layers and consequent failure of the composite membrane, it is important to accommodate such expansion of the coating metal layer in a controlled manner. As previously mentioned, it has been discovered that this expansion may be accommodated by (1) use of a flexible material for the intermediate layer; or by (2) use of a textured coating metal; or by a combination of both (1) and (2).

When accommodation of dimensional changes is attributable in whole or in part to the intermediate layer, that layer may generally be described as comprising porous, non-sintered materials, compounds, and complexes other than pure metals and metal alloys; it is preferably a material selected from thermally stable woven and non-woven fabrics, papers, and felts.

The intermediate layer may be from 1 to 500 µm in thickness and forms a continuous layer between the support matrix and the coating metal, and further serves to prevent contact between the base metal and the coating metal. The intermediate layer is porous or microporous, which allows hydrogen to flow both parallel and perpendicular to and through the plane of the layer relatively unimpeded.

The intermediate layer is chemically stable in the sense that under the conditions of use (at temperatures in the 200° to 1000° C. range), it does not react with the support matrix, the coating metal, or hydrogen to produce a layer comprising a compound, complex, or alloy that is substantially impermeable to hydrogen or to substantially reduce the tensile strength of the support matrix so as to compromise its utility. The intermediate layer is also thermally stable in the sense that it does not melt, sinter, or fuse at the elevated temperatures of use (200° C. to 1000° C.) to an extent that reduces the porosity of the layer, thereby to substantially increase its resistance to the flow of hydrogen.

Furthermore, when a flexible intermediate layer is used to accommodate expansion in the coating metal layer, it should be flexible in the sense that it is not brittle and lacks rigidity (i.e., it can be bent repeatedly to 180° with a radius of curvature of about 5 mm without cracking). Such flexibility is preferably retained following operation at elevated temperatures. The mechanical properties of the flexible intermediate layer allow it to be deformed, as by expanding or contracting ($\Delta L/L \geq 0.005$ where L is the length of the layer of material) without cracking or breaking. Such deformability may be achieved in a variety of ways. For example, fibers comprising the intermediate layer may be slidable with respect to adjacent fibers. Alternatively, fibers of the intermediate layer may be corrugated so as to allow expansion and contraction without rupture.

The chemical composition of the intermediate layer may be described as ceramic and glass fibers; the oxides of aluminum, silicon, boron, calcium, magnesium, and mixtures thereof; nitrides and carbides of boron; nitrides, carbides, and borides of silicon and aluminum; oxides, sulfides, carbides, borides, and nitrides of all of the Lanthanide metals, scandium, yttrium, molybdenum, tungsten, and all of the Group IVB and VB metals; silicides of all of the Group IVB and VB metals, and of scandium, yttrium, and all of the Lanthanide metals; zeolites; carbon; and chemically and thermally stable mixtures containing $\geq 50\%$ of such materials, compounds, and complexes. Preferred exemplary woven fabrics include fiberglass cloth, 3M's NEXTEL, zirconia cloth types ZYW15 and ZYW30A (Zircar Products, Inc. of Florida, New York), and SILTEMP 84CH (Ametek, Inc. of Wilmington, Del.). Examples of preferred non-woven fabrics, papers, and felts include APA-1, APA-2, APA-3, AS-1260, Type ZYF, Type D, and Type 99 (all from Zircar Products).

An important characteristic of the flexible intermediate layer is that it comprises a non-sintered material. The term "non-sintered" means that the material comprising the intermediate layer does not become a substantially isotropic, sintered composition either prior to or during fabrication of the composite metal membrane or after 1000 hours under operating conditions. The term "sintering" is common to the art of fabricating ceramic materials from powders and, in general, refers to a multi-step thermal densification process. See *Kirk-Othmer Encyclopedia of Chemical Technology*, page 265 (1979). In the first step of sintering on a micro scale, diffusion of material toward the points of contact among adjacent particles occurs, which initiates fusion between the particles. As high temperature (typically >1000° C.) is applied, fusion and coalescence takes place. The application of pressure to the mass to be sintered facilitates the process. As heating continues, particularly under applied pressure, the ceramic particles continue to fuse together and coalesce, eventually leading to fusion of the particles into a single ceramic piece, and ultimately eliminating all porosity from the ceramic mass. Sintering results in a material that is isotropic with respect to its mechanical properties. Sintering is generally undesirable for the intermediate layer of the composite membrane of the present invention because porosity is desirable and because sintering tends to yield an inherently brittle and inflexible structure which limits stretching (neighboring particles or fibers become fused and therefore can no longer slide past each other).

When the support matrix is a rigid metal, the intermediate layer serves to prevent contact between the coating metal layer and the metal support, thereby preventing interdiffusion of the metals which, in many cases, can lead to reductions as great as 95% in hydrogen flux through the membrane (see U.S. Pat. No. 5,259,870). The intermediate layer also serves to bridge gaps and smooth irregularities in the surface of the supporting metal matrix. In modules utilizing a rigid ceramic support matrix, the intermediate layer serves to bridge gaps in the surface, to smooth surface irregularities, and to protect the thin coating metal layer from damage should the rigid ceramic support matrix crack during use.

As previously mentioned, unwanted expansion of the coating metal layer may be accommodated by use of a textured coating metal. As used with respect to this invention, "textured" means closely spaced undulations, corrugations, ridges, ribs, dimples, lumps, or bumps in one or two dimensions. The coating metal layer is in contact with the intermediate layer, the latter being flexible or non-flexible. A woven or otherwise textured intermediate layer (flexible or non-flexible) may be utilized to impart texturing to the coating metal layer during the operation of the composite membrane. For instance, an intermediate layer such as woven glass, ceramic, or carbon cloth may serve as a template to impart substantially the same texturing to the coating metal layer in situ when the composite membrane is heated (to >200° C., preferably >500° C.) and simultaneously compressed ($\geq 200$ psig). The topography of the textured coating metal layer is preferably such that the spacing between the undulations, bumps, dimples, corrugations, ridges, etc. is from about 0.5 to about 100 times the coating layer thickness. The mean height of such texturing is preferably such as to allow displacement of the coating metal layer out of its primary plane. It has been observed that a mean height of at least 10% of the spacing between undulations, etc. is satisfactory.

The intermediate layer need not be flexible to accommodate the dimensional changes of the textured coating layer. It has been observed that a composite membrane having a textured coating metal layer that is cycled between expansion and contraction appears to develop dimensional changes through a multitude of small displacements of the coating metal layer at or near each undulation, etc. By way of contrast, it has been observed that a composite membrane having a non-textured coating metal layer that is similarly cycled between expansion and contraction develops dimensional changes that tend to accumulate in either a single or a few large "wrinkle" displacements of the coating metal layer, accompanied by the simultaneous appearance of holes at or near the "wrinkles," with attendant failure of the membrane.

Use of both a textured coating metal layer and a flexible intermediate layer has been found to be a particularly preferred embodiment of the present invention.

Figure 1A:
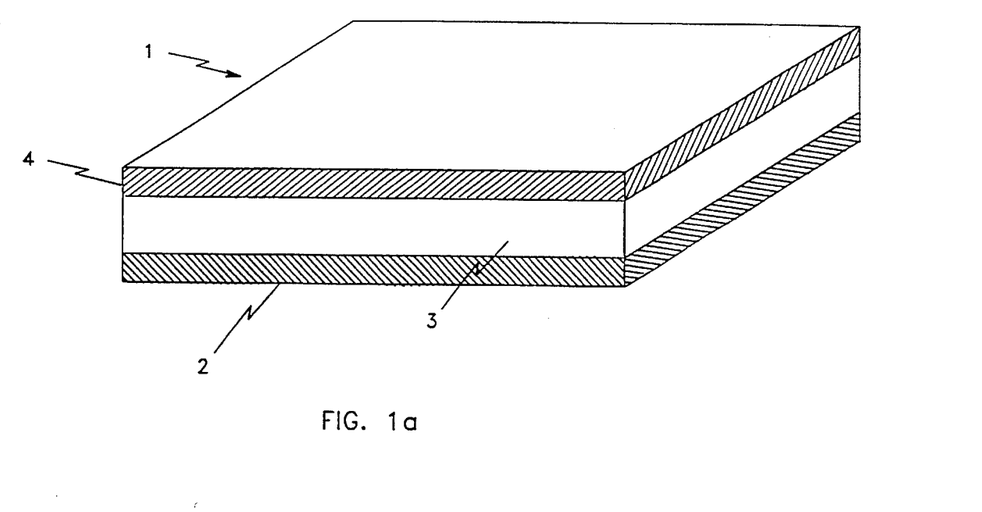
FIGS. 1a and 1b are schematic cross-sectional views of an exemplary composite membrane of the present invention.

Referring to FIG. 1a, there is shown a preferred exemplary embodiment of a three-layer composite membrane 1 comprising a support matrix 2, a flexible, non-sintered, porous or microporous intermediate layer 3, and a coating metal layer 4 (which may comprise two or more layers).

The composite metal membrane may be fabricated by placing the coating metal layer (in the form of a thin foil that is textured or smooth), the flexible intermediate layer, and the base metal layer in contact with each other and sealed into a test cell or module by means of a gasket placed between the cell or module and the coating metal layer, or by brazing or welding the assembled composite in place. The three layers become laminated to each other effectively in situ when they are heated to an elevated temperature and placed in a pressurized hydrogen-bearing feed stream fed to the cell or module. Alternatively, the coating and flexible layers are first laminated together by depositing the coating layer onto the flexible intermediate layer by electroless or electrolytic plating, chemical vapor deposition, plasma deposition, sputtering or thermal evaporation or spraying methods, followed by placing the so-laminated coating/flexible layer in contact with the base metal layer and securing the composite into a test cell or module as noted above.

When a textured coating metal layer is used, texturing may be applied thereto either in situ as explained above, or prior to assembly of the composite membrane, for example, by stamping or pressing a texturing pattern into the layer.

Figure 1B:
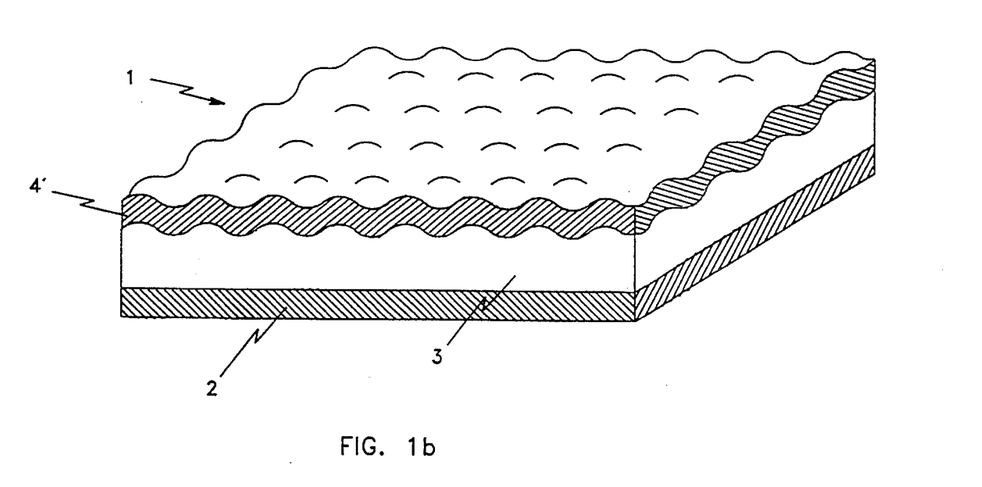

FIG. 1b shows a preferred embodiment of a three-layer composite membrane 1 comprising a support matrix 2, a flexible, non-sintered, porous or microporous intermediate layer 3, and a textured coating metal layer 4, (which may comprise two or more layers). Such an ordered arrangement of the texturing as shown in FIG. 1b is not essential, and the texturing may be randomly distributed over the coating metal layer.

In use, the composite hydrogen separation membrane of the present invention is typically incorporated into a module as a hydrogen separation element. Typical module configurations include a plate-and-frame configuration (shown in FIG. 3) and shell-and-tube configuration (shown in FIGS. 7–9).

Hydrogen separation modules include a feed inlet, permeate and raffinate outlets and a hydrogen separation element situated so that one side of the element is in contact with the feed stream and the second side is in contact with the permeate stream. Optionally, and for enhanced performance, the module may include a sweep stream inlet port that permits the flow of a gas or vapor sweep stream across the permeate side of the hydrogen separation element.

A gas-tight seal between the hydrogen separation element and the module is necessary to separate the impure feed gas from pure hydrogen permeate. Preferably a high-temperature gasket material, such as graphite (e.g., GRAFOIL® manufactured by Union Carbide), a soft metal such as copper, iron or nickel, asbestos or other metal oxide, or a composite of the same, such as graphite/metal or asbestos/metal may be used to achieve the gas-tight seal. In principle, soldering or welding could be employed, but gasketing offers several advantages, including ease of module fabrication, no significant introduction of contaminating metals into the composite metal membrane, and ease of membrane replacement. Graphite gaskets are very durable in non-oxidizing atmospheres up to 2000° C.

Figure 3:
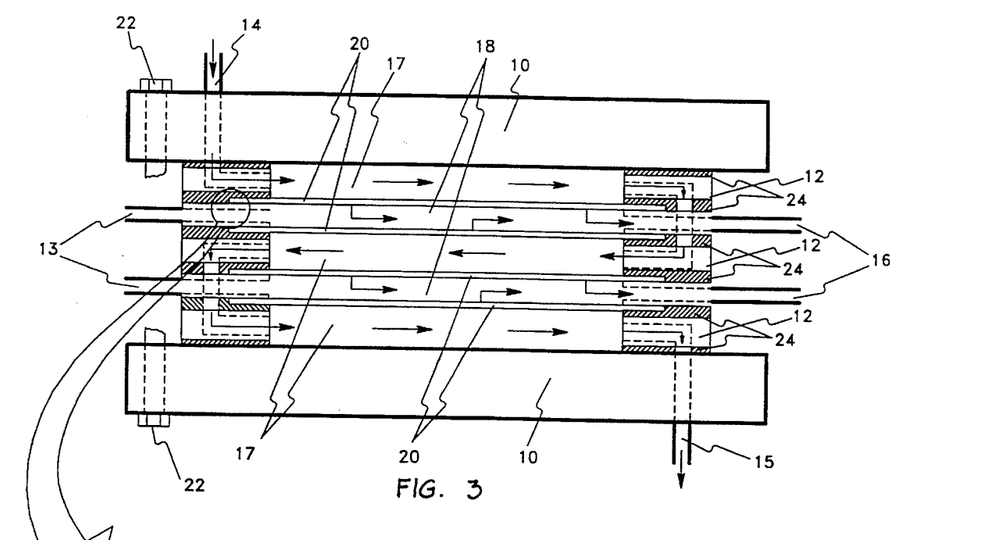
FIG. 3 is a cross-sectional view of a plate-and-frame module.

Referring again to the drawings, there is shown in FIG. 3 a cross-sectional schematic of a plate-and-frame module comprising spacers 12 stacked between end plates 10. The coating metal layer and intermediate layer (shown combined as one layer 20) are placed on the opposing surfaces of support matrix 18 and sealed to the module frame with gaskets 24. The entire module is held together with bolts 22. In operation, feed gas containing hydrogen enters the module through feed port 14 and flows over the exposed surface of the metal membranes via channels 17. Hydrogen permeates the metal membranes and enters the interior of support matrix 18, flows through the support matrix and is collected in permeate channels 16. Although the permeate channels are shown exterior to the module frame, the illustration is used primarily for clarity; they could also be incorporated as channels machined into spacers 12. A top view of the spacer 12 is shown in FIG. 3b which illustrates the void in the central portion of the spacer for passage of the feed stream. Optional sweep stream inlet ports 13 are shown in FIG. 3 for introducing a gas or vapor sweep stream to flow over the permeate side of the membrane. Finally, the feed gas, now depleted in hydrogen relative to the incoming feed stream, exits the module through raffinate port 15. The module is preferably operated at a temperature between 300° C. and 1000° C., with an especially preferred operating temperature range of 400° C. to 550° C. The module may be externally heated to the operating temperature, or it may be heated by flowing the feed gas through a preheater, the hot feed gas serving to maintain the module at the operating temperature.

Figure 3A:
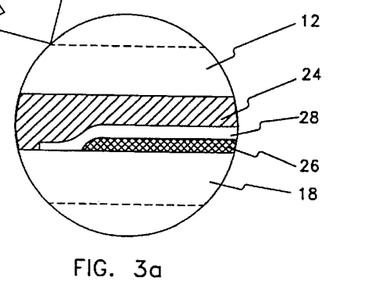
FIG. 3a is an enlarged cross-sectional view of a portion of FIG. 3, showing the position of gaskets.
Figure 3B:
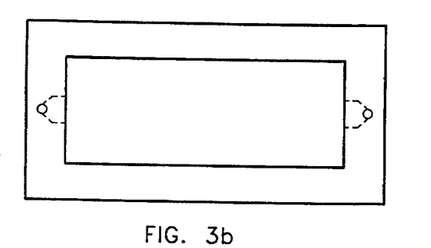
FIG. 3b is a top view of a spacer used to define the feed channel in a plate-and-frame module.

An enlarged view showing the position of the gaskets 24 is shown in FIG. 3a. Gaskets 24 seal to hydrogen-permeable coating metal layer 28 at the feed surface of the composite membrane. Between coating metal layer 28 and support matrix 18 is intermediate layer 26.

Preferred materials for use as the support matrix include stainless steel sheet or foil, perforated stainless steel sheet or foil, and mesh composed of fine metal wire. If the support matrix is a continuous non-broken plate or element (i.e., without holes, pores, perforations, slots, or other continuous openings through it), then it should not extend beyond the edge of the intermediate layer, and it is preferred that it be slightly smaller than the intermediate layer so that the intermediate layer extends over the edge of the support matrix. However, if the support matrix does contain holes, perforations, slots, or other continuous openings through it, then it may extend beyond the edges of the intermediate layer.

Figure 4:
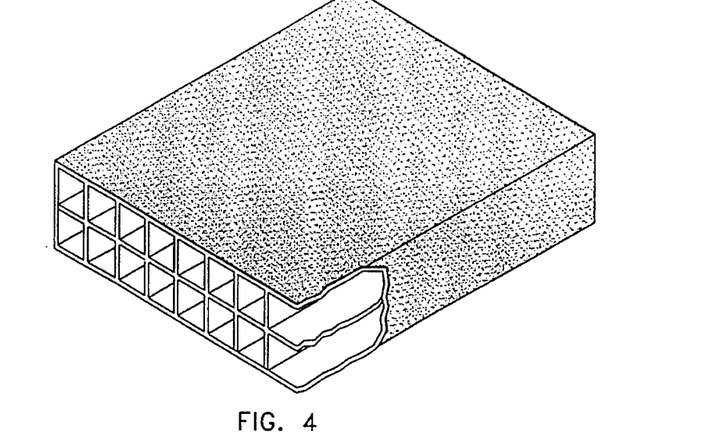
FIG. 4 is an end view of a plate-and-frame module support matrix showing channels in a porous ceramic monolith.

The support matrix may also comprise a porous ceramic structure containing a honeycomb-like array of rectangular channels running axially through the material, as shown in FIG. 4. One such ceramic form is the CELCOR® product line of cellular monoliths made and sold by Corning, Inc. In use, hydrogen passes through the coating metal and intermediate layers of the membrane, through the porous surface of the ceramic monolith where it collects in the rectangular channels, and is directed to the permeate collection tubes.

Figure 5:
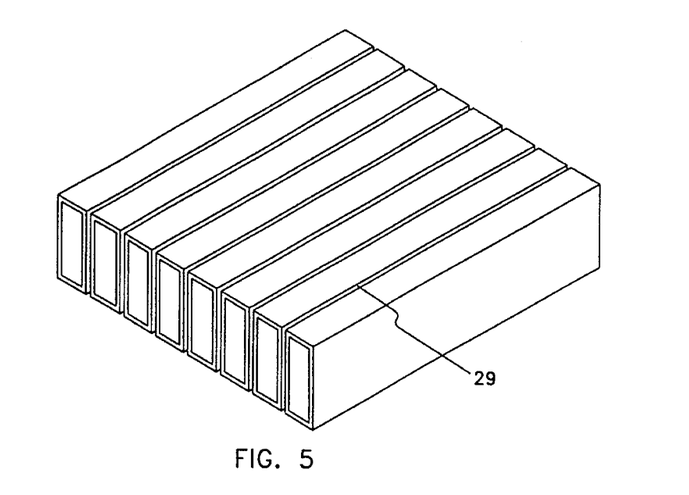
FIG. 5 is an end view of a plate-and-frame module support matrix showing channels formed by adjacent rectangular metal tubes.

Another example of a preferred support matrix is an array of rectangular metal tubes, as shown in FIG. 5. The tubes may be made of brass, steel, or stainless steel alloys, or any other metal with sufficiently high melting point and strength to resist crushing under operating conditions. In use, hydrogen passes through the metal membrane and is collected in the gaps 29 between the rectangular tubes. The hydrogen is then directed to the permeate collection tubes. The tubes may be perforated to allow hydrogen to collect within the tube channels before flowing to the permeate collection tubes.

Figure 6:
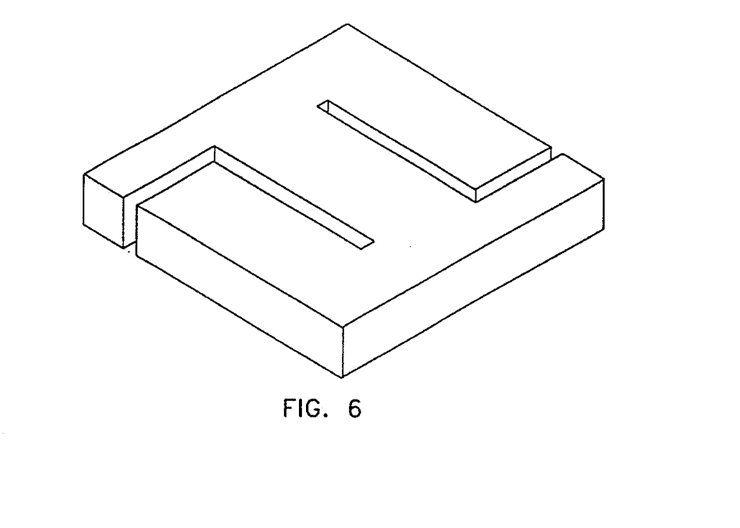
FIG. 6 is an end view of a plate-and-frame module support matrix showing slots in the support matrix to facilitate the flow of the permeate hydrogen.

Yet another example of a preferred support matrix is shown in FIG. 6 and consists of a metal plate with one or more slots (two are shown) cut into the plate to collect and facilitate the flow of the permeate hydrogen in the same manner as the spaces between the rectangular channels shown in the support matrix of FIG. 4.

Figure 7:
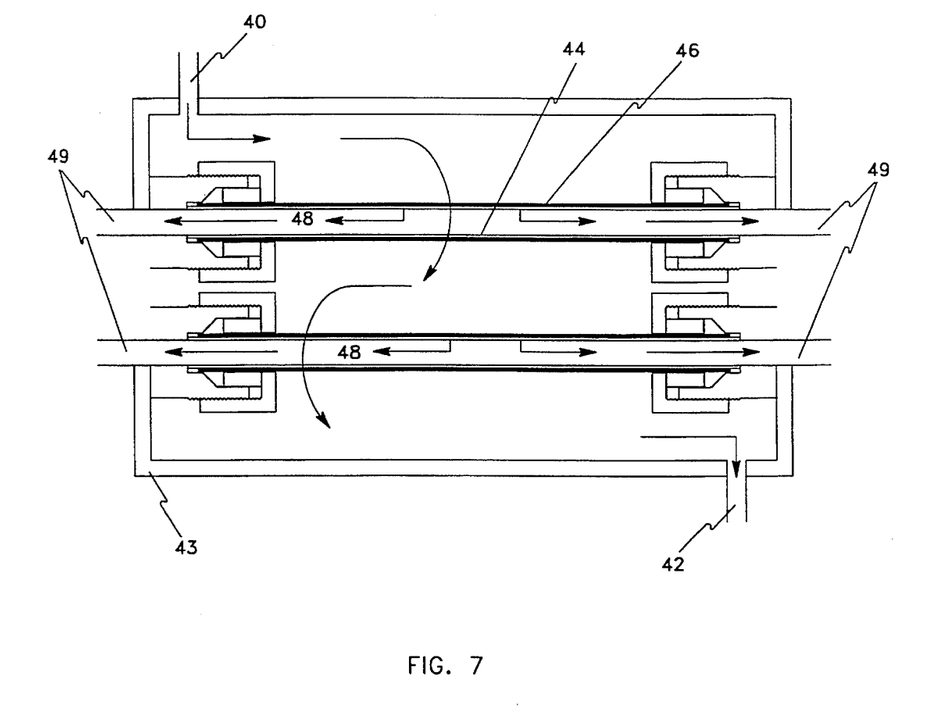
FIG. 7 is a cross-sectional view of a shell-and-tube module.

Use of the hydrogen separation element in a shell-and-tube module configuration is another exemplary embodiment of the invention. As FIG. 7 shows, the feed gas flows in through the feed port 40 and over the outer surface of the tubular composite metal membranes 44. Feed gas that is essentially depleted in hydrogen exits the module through the raffinate port 42. The thin hydrogen-permeable coating metal layers are supported on intermediate layers, which are in turn supported on metal tubes 46 (described in greater detail below). Hydrogen permeates the coating metal layers and flows to the interior of tube 48 where it is directed to permeate collection tubes 49. The entire module is enclosed in a shell 43 that is designed to withstand the feed pressure at the operating temperature.

The shell-and-tube module configuration is particularly useful when it is desired to pass a sweep stream (e.g., a sweep gas or vapor stream) over the permeate side of the tubular composite membrane. In such a case the sweep stream flows into one end of each membrane tube through the port or opening 49 (normally used to collect permeate hydrogen) and exits the opposite end of each membrane tube.

Figure 8A:
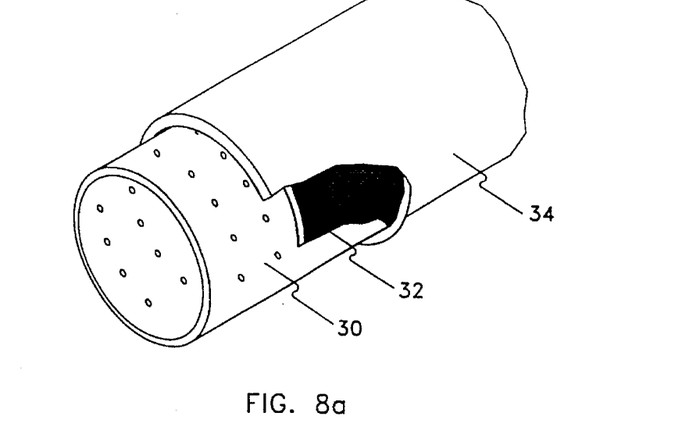
FIGS. 8a–8c are perspective views of various configurations of a shell-and-tube composite membrane element.
Figure 8B:
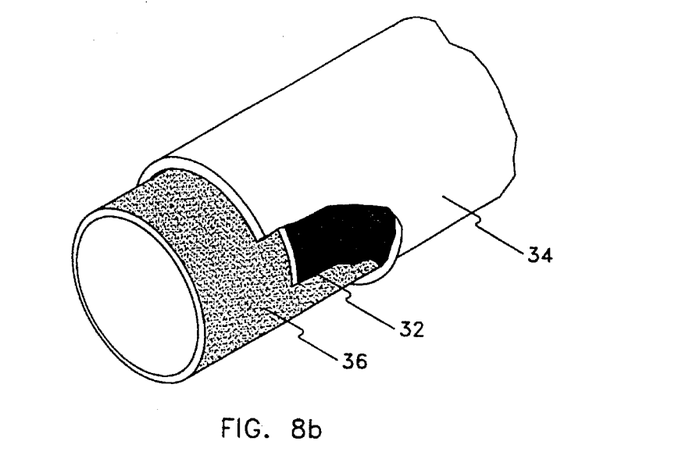
Figure 8C:
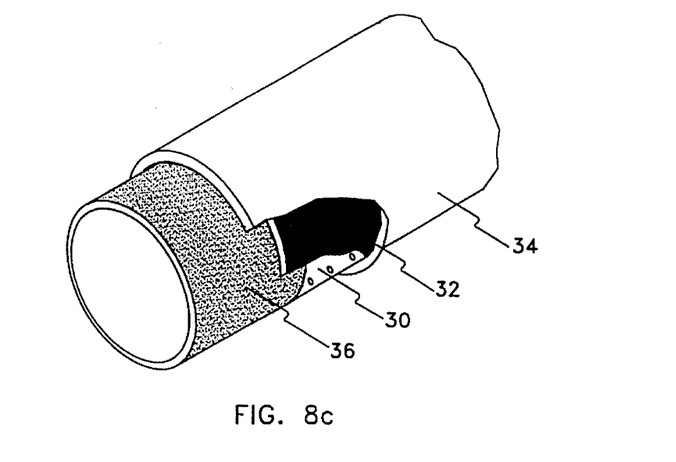

In the shell-and-tube configuration the support matrix is tubular. FIGS. 8a–c are breakaways illustrating various arrangements of the coating metal layer, the intermediate layer, and the support matrix of the composite metal membrane. FIG. 8a shows a perforated metal tube as the support matrix 30. Steel and stainless steel alloys are preferred materials for the support matrix. The intermediate layer 32 is wrapped around support matrix 30 and coating metal layer 34 is over the surface of intermediate layer 32. FIG. 8b shows an alternative embodiment in which the support matrix is a porous tube 36 comprising a porous ceramic or a porous sintered metal such as sintered stainless steel. A third embodiment is shown in FIG. 8c in which support matrix 36 is a perforated metal tube with porous metal tube sections welded or brazed to the end of the perforated tube; if intermediate layer 32 overlaps the porous tubular end pieces, the central portion of the tube-shaped support matrix need not be perforated, as hydrogen will flow through the porous intermediate layer, ultimately reaching the porous end pieces.

Figure 9:
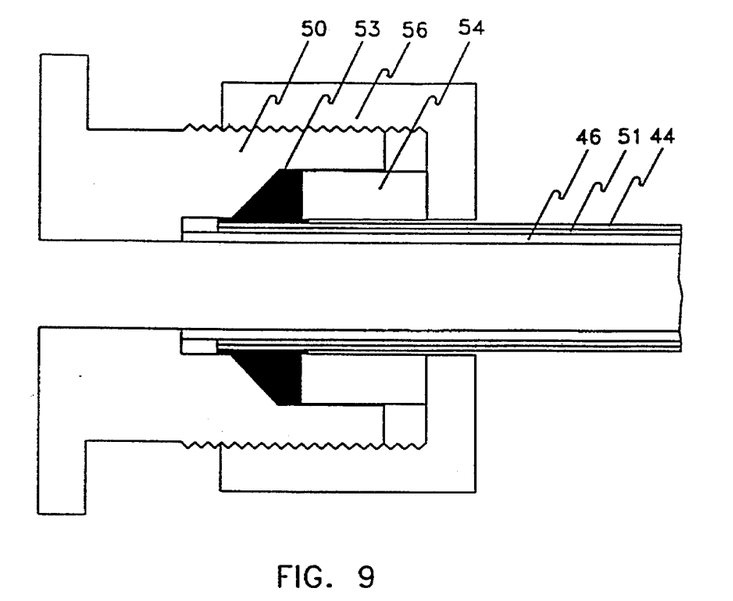
FIG. 9 is a cross-Sectional view of a shell-and-tube module showing a gasket securing the composite membrane of the present invention to the module.

FIG. 9 is an enlarged view of one end of a shell-and-tube module design showing gasket placement. Metal tube 46, which serves as the support matrix, with coating metal layer 44 and intermediate layer 51 wrapped around the metal tube, are inserted into a sleeve 50. A high-temperature gasket 53 such as graphite string or cord is compressed into sleeve 50 and seated against metal membrane 44 by forcing a ferrule 54 into sleeve 50 by nut 56 that threadingly engages sleeve 50 to enable it to exert force against ferrule 54 and gasket 53. Gasket 53 seals against coating metal layer 44 and sleeve 50, thereby preventing flow from the feed stream into the permeate stream. Sleeve 50 is preferably welded or brazed to the shell of the module.

Figure 10:
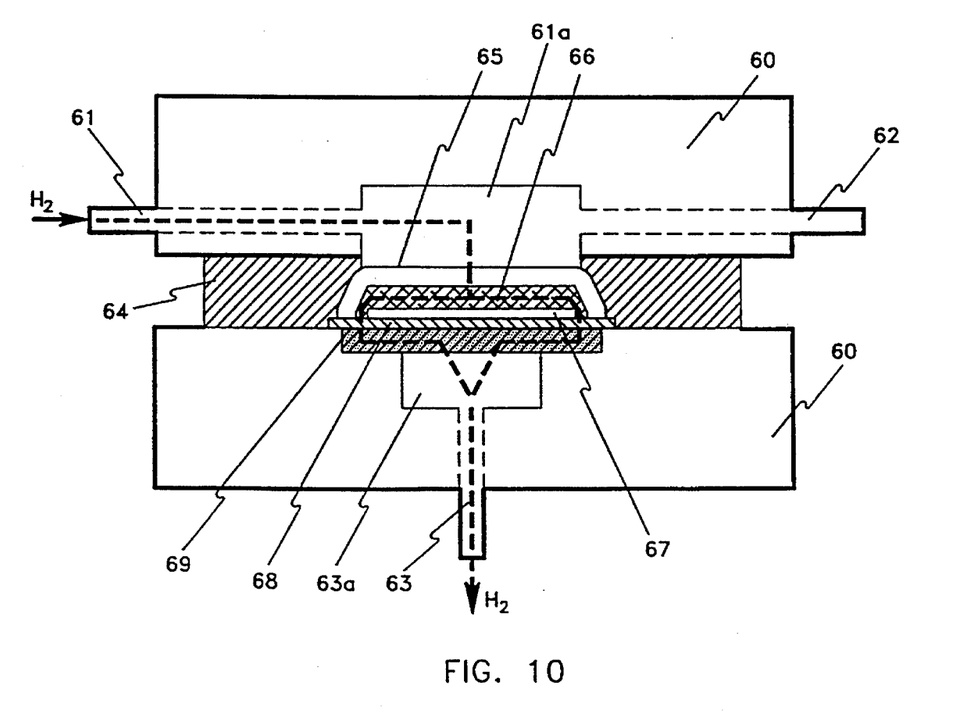
FIG. 10 is a cross-sectional view of a permeation test cell used to measure the performance of composite membranes of the present invention.

FIG. 10 is a cross-sectional view of a permeation test cell 60 showing the placement of a composite membrane of the present invention in the test cell. The two halves of the cell 60 are fitted with a feed inlet port 61, a feed plenum 61a, a raffinate port 62, a permeate plenum 63a and a permeate port 63. A grafoil gasket 64 seals the composite membrane into the cell, and seals to the surface of the Pd coating metal layer 65. A fabric intermediate layer 66 is placed between the Pd layer and a stainless steel support matrix 67. Combined layers 65, 66 and 67 form the composite metal membrane. To prevent intermetallic diffusion between the test cell 60 and the support matrix 67, and thus to permit reuse of the test cell, an aluminum oxide disc 68 is placed between the support matrix 67 and a sintered steel disc 69 which is part of the permeate half of the cell and also serves as a support element. The steel disc 69 serves to collect the permeate hydrogen as shown by the dotted line hydrogen pathway. This type of permeation cell was useful in demonstrating the functional properties of composite membrane that are the subject of this invention.

EXAMPLE 1

A three-layer Pd/NEXTEL fabric/316 stainless steel composite membrane was prepared and tested for hydrogen permeability in a test cell having the construction shown in FIG. 10. The composite membrane, about 3 cm in diameter, comprised a Pd coating layer 65, 25 µm thick and a dense (i.e., nonporous and nonperforated) support matrix 67 of type 316 stainless steel 50 µm thick separated by a continuous layer 66 of NEXTEL (an aluminum oxide/silicon oxide/boron oxide flexible woven fabric). The composite membrane was fabricated by layering Pd foil on the NEXTEL fabric, followed by placement of those two layers on the stainless steel foil. The composite membrane was then mounted in a steel permeation cell 60 of the configuration shown in FIG. 10, using a graphite gasket 64 to achieve a gas-tight seal to the membrane, effectively isolating the feed chamber of the cell from the permeate chamber of the cell so that only hydrogen diffusing through the membrane from the feed stream could enter the permeate stream. A sintered steel disc 69 at the permeate side of the composite membrane was used to collect the permeate hydrogen. Because the test cell was made of steel, in order to prevent fusion between the steel cell and the stainless steel support of the composite membrane and so be able to reuse the test cell, a thin, porous aluminum oxide filtration disc 68 (ANODISC from Whatman Scientific of Maidstone, England) was placed between the stainless steel support matrix 67 of the composite membrane and the test cell 60. The three layers of the composite membrane were laminated in situ by the operating temperature (400° C.) of the cell and the pressure (100 psig) of the feed stream. The composite membrane was tested for hydrogen permeability by measuring the flow rate of the permeate stream. As shown in FIG. 10, hydrogen gas is fed through feed inlet port 61 to feed plenum 61a, wherein it contacts and diffuses through the Pd coating metal layer 65, then hydrogen gas diffuses through fabric intermediate layer 66 and around support matrix 67, then through the ANODISC diffusion barrier disc 68, sintered steel disc 69, permeate plenum 63a and permeate outlet port 63.

The average hydrogen flux through the composite membrane was measured at 400° C. using a 99.95% pure hydrogen gas feed stream at 100 psig (780 kPa), the permeated hydrogen being at ambient pressure. The average hydrogen flux was 79 ft 3/ft 2. hr (24 $m^3/m^2$.hr).

EXAMPLE 2

Figure 2:
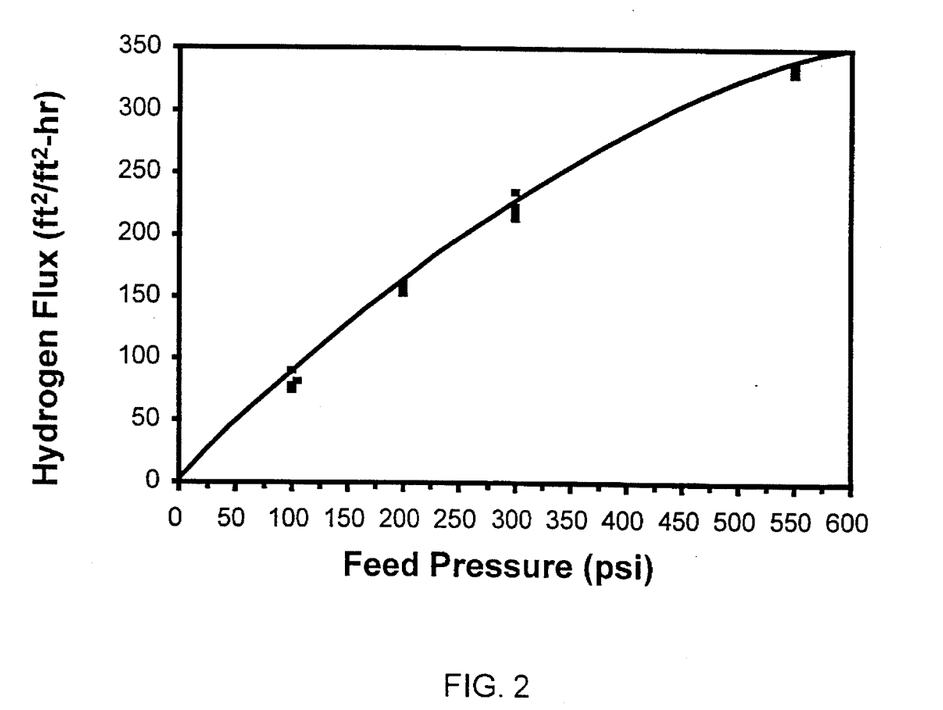
FIG. 2 is a plot of hydrogen flux versus feed pressure for a composite membrane of the present invention operated at 400° C.

Substantially the same composite membrane of Example 1 was tested for hydrogen permeability at 400° C. over a range of hydrogen gas feed pressure from 100 psig (780 kPa) to 550 psig (3843 kPa), with the permeate stream remaining at ambient pressure. Average flux through this membrane is shown plotted against the feed pressure in FIG. 2.

EXAMPLE 3

Substantially the same composite membrane of Example 1 was tested for hydrogen permeability at 400° C. over an extended period of time. The average initial flux was 75 $ft^3/ft^2$.hr (23 $m^3/m^2$.hr) and after 30 days' continuous operation at 400° C., the average hydrogen flux through the membrane was still the same.

EXAMPLE 4

Substantially the same composite membrane of Example 1, with the exception that the support matrix was nickel about 30 µm thick, was tested for hydrogen permeation. Average flux through this membrane was 71 $ft^3/ft^2$.hr (22 $m^3/m^2$.hr).

EXAMPLE 5

Substantially the same composite membrane of Example 1, with the exception that the support matrix was copper about 30 µm thick, was tested for hydrogen permeation. Average flux through this membrane at 400° C. was 62 $ft^3/ft^2$.hr (19 $m^3/m^2$.hr).

EXAMPLE 6

Substantially the same composite membrane of Example 1, with the exception that the intermediate-layer was SILTEMP 84CH (a silicon oxide fabric) about 350 µm thick, coated with an aluminum oxide slurry, was fabricated as in Example 1 with the exceptions noted herein. The aluminum oxide slurry was prepared by coating one side of the silicon oxide fabric with a suspension of aluminum oxide (DISPERAL by Condea of Germany) in methanol (1 g aluminum oxide in 2.5 mL methanol). Glycerol (0.5 g) was added to the suspension as a stabilizer to help keep the aluminum oxide particles suspended. The so-coated silicon oxide fabric was then dried in air and then heated to 700° C. in air to remove the organic residue from the aluminum oxide slurry coating. The aluminum oxide slurry coating, applied in this manner, filled the large voids in the silicon oxide textile and yielded a smooth, but porous, non-sintered surface.

The average flux through this membrane was measured at 600° C. over an extended period and initially was found to be 153 ft$^3$/ft$^2$.hr (47 m$^3$/m$^2$.hr), and the same after 15 days' operation.

EXAMPLE 7

Substantially the same composite membrane of Example 1, with the exception that the coating metal layer was silicon oxide-coated palladium about 25 μm thick, was tested for hydrogen permeation. The silicon oxide coating was microporous and was only on the surface of the palladium facing the feed stream, and was deposited on the palladium by plasma deposition. The thickness of the silicon oxide coating varied from about 0.1 to 1 μm. Average flux through this membrane at 400° C. was 30 ft$^3$/ft$^2$.hr (9.1 m$^3$/m$^2$.hr).

EXAMPLE 8

Substantially the same composite membrane of Example 1 was made, with the exception that the intermediate layer was a silicon oxide-based woven fabric (SILTEMP 84CH, from Ametek,Inc.) about 350 μm thick, and was tested for hydrogen permeation. Average flux through this membrane at 400° C. was 70 ft$^3$/ft$^2$.hr (21 m$^3$/m$^2$.hr).

EXAMPLE 9

Substantially the same composite membrane of Example 8 was prepared, with the exception that the support matrix layer was perforated stainless steel about 210 μm thick having a straight pattern of holes about 825 μm in diameter, rendering about 30% of the surface perforated. The membrane was tested for hydrogen permeation and exhibited an average flux of 70 ft$^3$/ft$^2$.hr (21 m$^3$/m$^2$.hr) at 400° C.

EXAMPLE 10

Substantially the same composite membrane of Example 1 was made, with the exception that the intermediate layer was fiberglass cloth (from McMaster-Carr Supply Co. of Los Angeles, Calif.) about 300 μm thick, and was tested for hydrogen permeation. Average flux through this membrane at 400° C. was 45 ft$^3$/ft$^2$.hr (14 m$^3$/m$^2$.hr).

EXAMPLE 11

Substantially the same composite membrane of Example 10 was made, with the exception that the support matrix layer was perforated stainless steel of the type described in Example 9, and was tested for hydrogen permeation. Average flux through this membrane at 400° C. was 90 ft$^3$/ft$^2$.hr (27 m$^3$/m$^2$.hr).

EXAMPLE 12

Substantially the same composite membrane of Example 9 was made, with the exception that the coating metal layer was an alloy of palladium with 5% iridium about 25 μm thick, and was tested for hydrogen permeation. Average flux through this membrane at 600° C. was 110 ft$^3$/ft$^2$.hr (34 m$^3$/m$^2$.hr).

EXAMPLE 13

Substantially the same composite membrane of Example 9 was made, with the exception that the coating metal layer was a Pd-25Ag alloy about 25 μm thick, and was tested for hydrogen permeation. Average flux through this membrane at 400° C. was 145 ft$^3$/ft$^2$.hr (44 m$^3$/m$^2$.hr) and at 600° C. was 206 ft$^3$/ft$^2$.hr (63 m$^3$/m$^2$.hr).

EXAMPLE 14

Substantially the same composite membrane of Example 1 was made, with the exception that the intermediate layer was aluminum oxide paper (type APA-3 from Zircar Products, Inc.) about 330 μm thick. Prior to fabricating the composite metal membrane, the aluminum oxide paper was calcined in air at 800° C. to remove organic binders. Average hydrogen flux through this membrane at 400° C. was 76 ft$^3$/ft$^2$.hr (23 m$^3$/m$^2$.hr).

EXAMPLE 15

Substantially the same composite membrane of Example 14 was made, with the exception that the intermediate layer was aluminum oxide felt (type APA-2 from Zircar Products) about 1000 μm thick as received and without compressing the fibers, and was tested for hydrogen permeation. Average flux through this membrane at 400° C. was 77 ft$^3$/ft$^2$.hr (23 m$^3$/m$^2$.hr).

Comparative Example

To illustrate the problems associated with the use of a sintered rigid ceramic support instead of flexible fabric as the intermediate layer in the composite metal membrane, a composite membrane was made by laminating a palladium-nickel (nominally 25% palladium and 75% nickel) coating metal layer about 20 μm thick over a rigid porous aluminum oxide intermediate layer (ANODISC from Whatman Scientific of Maidstone, England) having a much smaller coefficient of thermal expansion than the stainless steel used to fabricate the permeation cell. The combined palladium-nickel/aluminum oxide layers were placed on a support matrix of sintered stainless steel and tested for hydrogen permeability at 500° C. as described in Example 1. However, due to an excessively high hydrogen flow rate, no initial flux measurement could be made. A leak test was conducted using argon at 100 psig (780 kPa). The argon flow rate through the permeate line was also too high to measure, indicating a large leak from the feed stream to the permeate stream.

Upon cooling and dismantling the permeation cell, the membrane was found to be broken into many pieces. The aluminum oxide intermediate layer was observed to be fractured, apparently causing the fracture of the palladium-nickel coating metal.

EXAMPLE 16

A plate-and-frame module of substantially the same design as depicted in FIG. 3 was fabricated in the following manner. The spacer plates 12 and end plates 10 were machined from type 304 stainless steel. The spacer plates were 3.2 cm thick, 10.2 cm wide and 25.4 cm long. The end plates were 3.2 cm thick, 15.2 cm wide, and 30.5 cm long. The perimeter of the end plates were drilled to accept fourteen 1.3-cm-long, grade 8 steel bolts. The spacer plates 12 were of the design shown in FIG. 3B. The support matrices 18 were of the same over-all dimensions as the spacer plates and were made from stainless steel plate with two slots cut into the plates in the same fashion as the support matrix shown in FIG. 6. The module accommodated four composite membranes with a total exposed membrane area of 360 cm².

The membranes were made in pairs by placing a piece of SILTEMP 84CH fabric approximately 7.0 cm× 20.3 cm, which served as the intermediate layer 26, on each of the two opposing surfaces of the permeate spacer plate 12. Over each piece of silicon oxide fabric was placed the coating metal layer 28 consisting of a piece of metal foil 25 μm×7.7 cm×21 cm, the metal foil comprising a Pd-25Ag alloy. A Grafoil gasket 24 was placed between the Pd-25Ag foil and the opposing feed spacer or end plate in such a manner as to form a gas-tight seal between the Pd-25Ag foil and the spacers, thereby preventing feed gas from flowing directly from the feed side of the membrane to the permeate side of the membrane. The composite membrane was laminated in situ during operation.

The module was equipped with a feed inlet port 14 in one end plate and a raffinate exit port 15 in the other end plate so that the feed stream could flow through a continuous path over the feed side surfaces of all four membranes in series (i.e., sequentially), and then exit the module. The permeate hydrogen was collected from each pair of membranes into two permeate channels 18 and directed out of the module via stainless steel tubing 16.

After heating the module to 400° C. its operation was demonstrated by flowing 99.95% pure hydrogen into the feed side of the module at 100 psig (780 kPa), the permeated hydrogen exiting the module at ambient pressure. The average flux was 145 ft³/ft².hr (44 m³/m².hr).

EXAMPLE 17

Substantially the same module of Example 16 was made, with the exception that the support matrix was a plurality of rectangular brass tubes (0.3 cm×0.6 cm) laid side by side as shown in FIG. 5 and the coating metal layer was Pd foil 75 μm thick, and was tested for hydrogen permeation. Average flux through this module at 400° C. was 19 ft³/ft².hr (5.8 m³/m².hr).

EXAMPLE 18

Substantially the same module of Example 16 was made, with the exception that the support matrix was a steel plate with a narrow gap near the edge of the intermediate layer and the coating metal layer was Pd foil 25 μm thick, and was tested for hydrogen permeation. Average flux through this module at 400° C. was 55 ft³/ft².hr (17 m³/m².hr).

EXAMPLE 19

Substantially the same module of Example 18 was made, with the exception that the coating metal layer was a Pd-25Ag alloy foil 25 μm thick, and was tested for hydrogen permeation. Average flux through this module at 400° C. was 80 ft³/ft².hr (24 m³/m².hr).

EXAMPLE 20

Substantially the module of Example 17 was made, with the exception that the intermediate layer was NEXTEL fabric about 250 μm thick, and was tested for hydrogen permeation. Average flux through this module at 400° C. was 150 ft³/ft².hr (45 m³/m².hr).

EXAMPLE 21

Substantially the same model of Example 20 was made and tested with the exception that the hydrogen feed side pressure was 590 psig (permeate side at ambient pressure). The module was heated from ambient temperature to 400° C., and average flux therethrough was 390 ft³/ft².hr (117 m³/m².hr). After operation for 48 hours, the module was cooled and disassembled. The Pd-25Ag coating layer was corrugated along both axes, yielding a dimpled appearance, mirroring the texture of the NEXTEL fabric. The mean distance between the peaks of the corrugations was about 1 mm.

EXAMPLE 22

Substantially the same module of Example 20 was made and tested except that the spacer plates 12 were each fitted with four stainless steel square rods or baffles (3.2 cm tall×3.2 cm wide×5.1 cm long) placed at equal intervals along the length of the feed channel 17. The square rods or baffles served to improve mixing of the feed stream over the feed surface of the membrane. The hydrogen flux through this module at 300° C., 100 psig hydrogen feed and ambient pressure permeate was 98 ft³/ft².hr (29 m³/m².hr).

To determine the effectiveness of the baffled feed channel 17, a mixed gas feed stream containing 40% carbon dioxide and 60% hydrogen was passed through the feed channel of the module at 75 psig and 300° C. The hydrogen flux was 31 ft³/ft².hr (9.3 m³/m³. hr) at 66% hydrogen recovery and 13 ft³/ft².hr (3.9 m³/m².hr) at 85% hydrogen recovery. These experimental fluxes were in good agreement with theoretical values, indicating that the baffles in the feed channel promote gas-phase mixing at the feed surface of the membrane.

EXAMPLE 23

Substantially the same module of Example 22 was made and tested with a mixed gas feed having the same composition as in Example 22, with the exception that the coating metal layer was Pd foil 75 μm thick. At 400° C. and with the feed pressure at 300 psig (permeate at ambient pressure), the hydrogen flux was 42 ft³/ft².hr (13 m³/m².hr) at 65% hydrogen recovery and 28 ft³/ft².hr (8.4 m³/m².hr) at 85% hydrogen recovery. Again, these experimental fluxes were in good agreement with the theoretical values, indicating that the baffled feed spacers promote efficient gas-phase mixing at the feed side of the membrane.

EXAMPLE 24

Substantially the same module of Example 21 was made and tested, except that soft (annealed) copper gaskets were used in place of Grafoil gaskets. Average fluxes through this module at 400° C. (400 psig hydrogen feed and ambient pressure permeate) and at 300° C. (100 psig feed and ambient pressure permeate) were 265 ft³/ft².hr (80 m³/m².hr) and 94 ft³/ft².hr (28 m³/m².hr), respectively.

The terms and expressions employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A composite hydrogen separation element comprising, after fabrication, a nonporous hydrogen-permeable coating metal layer supported by a rigid support matrix, a flexible, porous, non-sintered, non-metallic intermediate layer between said coating metal layer and said support matrix, wherein, at a temperature of from about 200° C. to about 1000° C., said intermediate layer does not chemically react with hydrogen or with said coating metal layer or with said support matrix to form a hydrogen-impermeable layer, and said support matrix does not react with hydrogen or with said intermediate layer to substantially reduce the tensile strength of said support matrix.

2. A composite hydrogen separation element comprising, after fabrication, a nonporous hydrogen-permeable textured coating metal layer, said coating metal layer supported by a rigid support matrix, and a porous, non-metallic intermediate layer between said textured coating metal layer and said support matrix, wherein, at a temperature of from about 200° C. to about 1000° C., said intermediate layer does not chemically react with hydrogen or with said textured coating metal layer or with said support matrix to form a hydrogen-impermeable layer, and said support matrix does not react with hydrogen or with said intermediate layer to substantially reduce the tensile strength of said support matrix.

3. The composite hydrogen separation element of claim 2 wherein said intermediate layer is flexible and non-sintered.

4. The hydrogen separation element of claim 1 or 3 wherein said intermediate layer is a fabric.

5. The hydrogen separation element of claim 4 wherein said fabric is selected from woven and non-woven.

6. The hydrogen separation element of claim 4 wherein said fabric is selected from a paper and a felt.

7. The hydrogen separation element of claim 5 wherein said intermediate layer is a woven fabric comprising woven fibers of a material selected from aluminum oxide, silicon oxide, mixtures containing $\geq 50\%$ aluminum oxide and silicon oxide, zirconium oxide, titanium oxide, yttrium oxide, hafnium oxide, vanadium oxide, niobium oxide, tantalum oxide, silicate glasses, borate glasses, carbon, and mixtures thereof.

8. The hydrogen separation element of claim 5 wherein said intermediate layer is a non-woven fabric comprising non-woven fibers of a material selected from aluminum oxide, silicon oxide, mixtures containing $\geq 50\%$ aluminum oxide and silicon oxide, zirconium oxide, titanium oxide, yttrium oxide, hafnium oxide, vanadium oxide, niobium oxide, tantalum oxide, silicate glasses, borate glasses, carbon, and mixtures thereof.

9. The hydrogen separation element of claim 6 wherein said paper or felt is predominantly composed of fibers of a material selected from silicon dioxide, aluminum oxide, zirconium oxide, titanium oxide, yttrium oxide, hafnium oxide, vanadium oxide, niobium oxide, tantalum oxide, silicate glasses, borate glasses, carbon, and mixtures thereof.

10. The hydrogen separation element of claim 2 wherein said intermediate layer comprises a material selected from aluminum oxide, silicon oxide, mixtures containing $\geq 50\%$ aluminum oxide and silicon oxide, zirconium oxide, titanium oxide, yttrium oxide, hafnium oxide, vanadium oxide, niobium oxide, tantalum oxide, silicate glasses, borate glasses, carbon, and mixtures thereof.

11. The hydrogen separation element of claims 1 or 2 or 3 wherein said support matrix is a material selected from ceramic, metal and carbon.

12. The hydrogen separation element of claims 1 or 2 or 3 wherein said support matrix is ceramic and is in a form selected from a plate, a tube and a monolith having a honeycomb-like cross-section.

13. The hydrogen separation element of claims 1 or 2 or 3 wherein said support matrix is metal and is in a form selected from a perforated sheet, a non-perforated sheet, a slotted sheet, a tube, a mesh, a porous sheet and a nonporous sheet.

14. The hydrogen separation element of claim 13 wherein said support matrix is in the form of a tube that is in a form selected from mesh, perforated, non-perforated, slotted, porous and nonporous.

15. The hydrogen separation element of claims 1 or 2 or 3 wherein said support matrix is a hydrogen-permeable metal in the form of a sheet or a tube.

16. The hydrogen separation element of claims 1 or 2 or 3 wherein said intermediate layer comprises a material selected from a metal oxide, a metal carbide, a metal nitride, a metal sulfide, and mixtures thereof.

17. The hydrogen separation element of claims 1 or 2 or 3 wherein said coating metal layer is a hydrogen-permeable metal selected from a transition metal, alloys and composites thereof, said coating metal layer being chemically and physically stable at temperatures of at least 200° C.

18. The hydrogen separation element of claim 17 wherein said coating metal layer is selected from the group consisting essentially of the transition metals from Groups VIIB and VIIIB of the Periodic Table, and alloys containing $\geq 20$ wt % of said metals.

19. The hydrogen separation element of claim 18 wherein said coating metal layer is selected from the group consisting essentially of Fe, Mn, Ni, Pd, Pt and Ru.

20. The hydrogen separation element of claim 19 wherein said coating metal is smooth.

21. The hydrogen separation element of claim 19 wherein said coating metal is textured.

22. The hydrogen separation element of claim 21 wherein said intermediate layer is woven or textured and said coating metal is textured by pressing said coating metal in the form of a foil onto said intermediate layer.

23. The hydrogen separation element of claim 21 wherein said intermediate layer is woven or textured and said coating metal is textured by depositing it on said intermediate layer by a process selected from chemical vapor deposition, electrolytic deposition, electroless deposition, plasma deposition, thermal evaporation, thermal spraying, and sputtering.

24. A hydrogen separation module comprising a housing that has a feed inlet, a permeate outlet, a raffinate outlet and at least one hydrogen separation element which, after fabrication, comprises a nonporous hydrogen-permeable coating metal layer supported by a rigid ceramic, carbon, or metal support matrix, and a flexible porous intermediate layer between said coating metal layer and said support matrix, wherein, at a temperature of from about 200° C. to about 1000° C., said intermediate layer does not chemically react with hydrogen or with said coating metal layer or with said support matrix to form a hydrogen-impermeable layer, and said support matrix does not react with hydrogen or with said intermediate layer to substantially reduce the tensile strength of said support matrix.

25. A hydrogen separation module comprising a housing that has a feed inlet, a permeate outlet, a raffinate outlet and at least one hydrogen separation element comprising, after fabrication, a nonporous hydrogen-permeable textured coating metal layer, said coating metal layer supported by a rigid support matrix, and a porous, non-metallic intermediate layer between said textured coating metal layer and said support matrix, wherein, at a temperature of from about 200° C. to about 1000° C., said intermediate layer does not chemically react with hydrogen or with said textured coating metal layer or with said support matrix to form a hydrogen-impermeable layer, and said support matrix does not react with hydrogen or with said intermediate layer to substantially reduce the tensile strength of said support matrix.

26. The module of claim 24 or 25 in a plate-and-frame configuration.

27. The module of claim 24 or 25 in a shell-and-tube configuration.

28. The module of claim 24 wherein said coating metal layer of said at least one hydrogen separation element is textured.

29. The module of claims 24 or 25 or 28, further including a sweep stream inlet port that permits the flow of a sweep stream across the permeate side of said at least one hydrogen separation element.

30. The module of claims 24 or 25 or 28, further including at least one means for securing said hydrogen separation element to said housing and for substantially isolating said feed inlet from said permeate outlet.

31. The module of claim 30 wherein said at least one means is selected from a braze, a weld and a gasket.

32. The module of claim 31 wherein said at least one means is a gasket and is metallic or non-metallic.

33. The module of claim 32 wherein said gasket is graphite.

34. The module of claim 32 wherein said gasket is copper.

* * * * *